(12) United States Patent
Esser et al.

(10) Patent No.: US 6,232,468 B1
(45) Date of Patent: May 15, 2001

(54) DIPEPTIDES WITH NEUROKININ-ANTAGONISTIC ACTIVITY

(75) Inventors: Franz Esser, Ingelheim/Rhein; Gerd Schnorrenberg, Gau-Algesheim; Hans-Peter Ignatow; Günther Giesler, both of Ingelheim/Rhein; Birgit Jung, Schwabenheim; Georg Speck, Ingelheim/Rhein, all of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/451,894

(22) Filed: Dec. 1, 1999

Related U.S. Application Data

(63) Continuation of application No. 08/743,805, filed on Nov. 5, 1996, now abandoned.

(30) Foreign Application Priority Data

Nov. 6, 1995 (DE) .............................................. 195 41 283

(51) Int. Cl.[7] ...................... C07D 241/86; C07D 241/02; C07D 209/02; A61K 31/517; A61K 31/403; A61N 29/00
(52) U.S. Cl. ................... 544/355; 514/252.13; 514/414; 544/372; 548/467
(58) Field of Search ............................ 548/467; 544/355, 544/372; 514/414

(56) References Cited

U.S. PATENT DOCUMENTS

| | | | |
|---|---|---|---|
| 5,596,000 | 1/1997 | Esser et al. .......................... | 514/312 |
| 5,616,620 | 4/1997 | Rudolf et al. ........................ | 514/620 |
| 5,712,273 | 1/1998 | Schnorrenberg et al. ........... | 514/218 |
| 5,849,918 | 12/1998 | Esser et al. ......................... | 546/157 |

FOREIGN PATENT DOCUMENTS

WO94 05693 A1    3/1994 (WO).

OTHER PUBLICATIONS

Hagiwara, D. et al; Journal of Medicinal Chemistry, 1994, 37, 2090–2099.

*Primary Examiner*—Floyd D. Higel
(74) *Attorney, Agent, or Firm*—Robert P. Raymond; Alan R. Stempel; Mary-Ellen M. Devlin

(57) ABSTRACT

Disclosed are compounds which are neurokinin (tachykinin)-antagonists, useful for the treatment or prevention of inflammatory and allergic disease. A representative compound is:

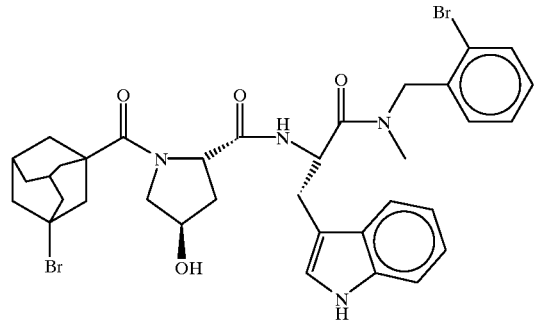

5 Claims, No Drawings

DIPEPTIDES WITH NEUROKININ-ANTAGONISTIC ACTIVITY

RELATED APPLICATIONS

This application is a continuation of Ser. No. 08/743,805, filed Nov. 5, 1996, now abandoned.

The invention relates to new amino acid derivatives of general formula I $$R^1-R^{11}-A^1-A^2-NR^2R^3 \quad (I)$$

and the pharmaceutically acceptable salts thereof, processes for preparing them and pharmaceutical compositions containing these compounds. The compounds are valuable neurokinin (tachykinin)-antagonists.

European Patent Applications EP 394 989 and EP 443 132 and WO 94/05693 describe peptides having a neurokinin antagonistic activity. The compounds according to the invention differ from these compounds essentially in the components $R^1$, $A^2$, $R^5$ and $NR^2R^3$.

The abbreviations used for the amino acids in this specification and in the claims correspond to the usual three-letter code as described, for example, in Europ. J. Biochem., 138, 9 (1984). The other abbreviations are explained as follows:

| | |
|---|---|
| Boc | = t-butoxycarbonyl |
| Bzl | = benzyl |
| CDI | = carbonyldiimidazole |
| Cha | = 3-cyclohexylalanine |
| DCCI | = dicyclohexylcarbodiimide |
| DCH | = dicyclohexylurea |
| HOBt | = 1-hydroxybenzotriazole |
| Hpa | = homophenylalanine |
| Hyp | = (2S,4R)-hydroxyproline |
| Pal | = 3-(1-pyrrolyl)alanine |
| THF | = tetrahydrofuran |
| TFA | = trifluoroacetic acid |
| Z | = benzyloxycarbonyl |
| Me | = methyl |
| Ac | = acetyl |
| Et | = ethyl |
| DMF | = dimethylformamide |
| DPPA | = diphenylphosphorylazide |
| PPA | = polyphosphoric acid |
| RT | = room temperature |
| Mtr | = 4-methoxy-2,3,6-trimethylbenzene sulphonyl |
| Trp(for) | = formyl-protected tryptophan |
| Met(0) | = methionine in which S is oxidised to form the sulphoxide |
| Bum | = N(π)-tert · butoxymethyl |

The term amino acid (unless expressly stated otherwise in the text which follows) covers natural and unnatural amino acids, both the D- and the L-forms, particularly α-amino acids, and the isomers thereof.

If an amino acid is given without a prefix, this denotes the L-form of the amino acid. The D-form is specifically given.

A simplified representation is used for the formulae. When representing the compounds, all the $CH_3$ substituents are indicated by a dash, thus, for example:

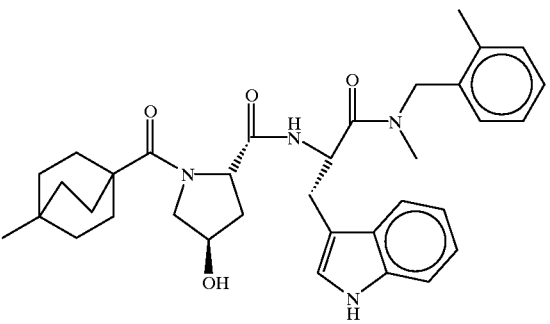

denotes

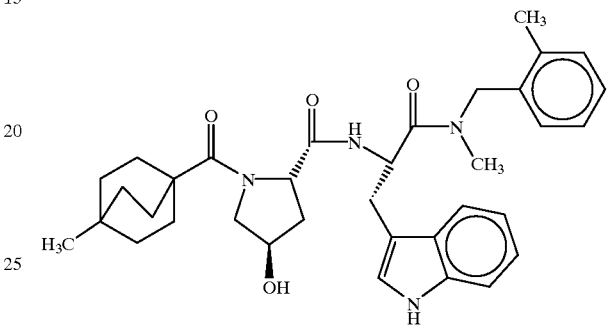

The invention relates to new amino acid derivatives of general formula I $$R^1-R^{11}-A^1-A^2-NR^2R^3 \quad (I)$$

and the pharmaceutically acceptable salts thereof, wherein
$R^1$ is (a) adamantyl or noradamantyl which is unsubstituted or substituted by $X^1$ or by one or 2 oxo groups, wherein $X^1$ denotes halogen, COOH, $C(O)NH_2$, C(O)Oalkyl, C(O)NHalkyl, $C(O)N(alkyl)_2$ [wherein alkyl denotes methyl, ethyl, propyl, butyl or pentyl],

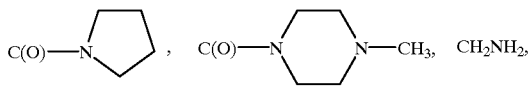

$CH_2$, NH-alkyl, $CH_2N(alkyl)_2$ [wherein alkyl denotes methyl, ethyl, propyl, butyl or pentyl],

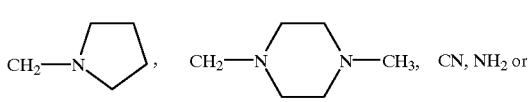

NH(Sch) [wherein Sch denotes methyloxycarbonyl, ethyloxycarbonyl or phenyl ($C_{1\ or\ 2}$-alkyl)oxycarbonyl, in which the phenyl is unsubstituted or substituted by halogen, $(C_{1-5})$ alkyl or $(C_{1-5})$alkoxy]; or (b) a saturated 6-membered ring having 6 carbon atoms or 5 carbon atoms and one N-atom, which has a $-CH_2-CH_2-$ bridge between two carbon atoms in the p-position, which is unsubstituted or substituted by $X^2$ and/or one or two oxo groups; wherein $X^2$ denotes halogen, alkyl, OH, $-O$-alkyl, $-C(O)Oalkyl$, $-COOH$, $-C(O)NH_2$, $-C(O)NHalkyl$, $-C(O)N(alkyl)_2$ [wherein alkyl denotes methyl, ethyl, propyl, butyl or pentyl], CN, $NH_2$ or NH(Sch) [wherein Sch denotes methyloxycarbonyl, ethyloxycarbonyl or phenyl ($C_{1\,or\,2}$-alkyl)oxycarbonyl, in which the phenyl is unsubstituted or substituted by halogen, $(C_{1-5})$alkyl or $(C_{1-5})$alkoxy]; or (c) one of the rings

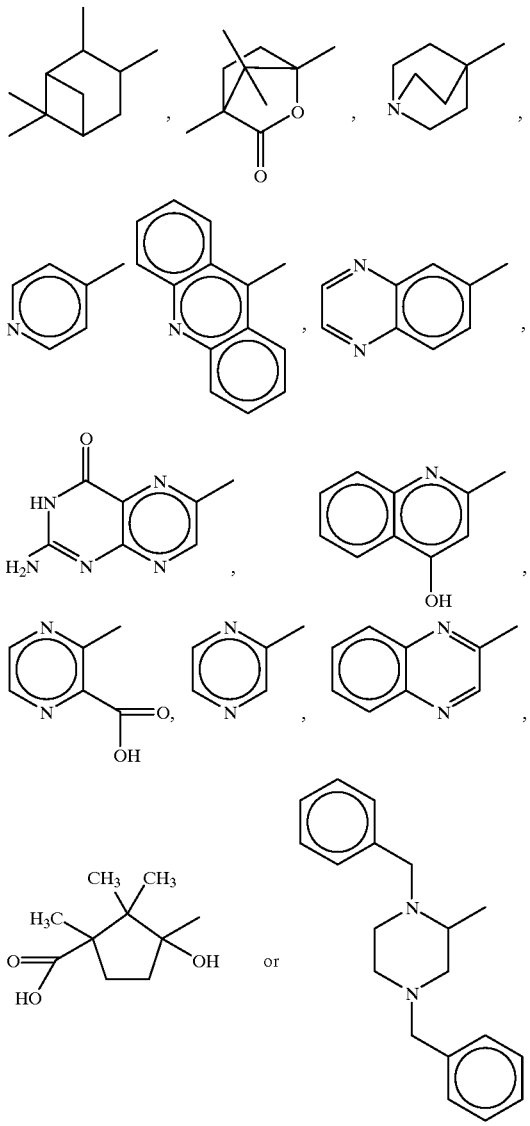

(d) if $R^{11}$ is —C($C_5H_{10}$)—C(O)—, $R^1$ can represent phenyl;

$R^{11}$ denotes
—C(O)—, —CH$_2$—C(O)—, —C($C_5H_{10}$)—C(O)—, —NH—C(O)— or O—C(O)—;

$A^1$ denotes

D- or L-serine (Ser), D- or L-threonine (Thr), D- or L-allothreonine, D- or L-proline (Pro), D- or L-didehydroproline (ΔPro) such as, for example, 3,4-didehydroproline (Δ(3,4)-Pro), D- or L-hydroxyproline (Pro (OH)) such as for example 3-hydroxyproline (Pro(3OH)) and 4-hydroxyproline (Pro(4OH)), D- or L-thiazolidine-4-carboxylic acid, D- or L-aminoproline (Pro(NH$_2$)) such as for example 3-aminoproline (Pro(3NH$_2$)) and 4-aminoproline (Pro(4NH$_2$)), D- or L-pyroglutamic acid (pGlu), D- or L-hydroxypiperidinocarboxylic acid such as, for example, 5-hydroxypiperidino-2-carboxylic acid, in which any hydroxy and amino groups contained therein may be protected by conventional protecting groups (e.g. acyl, carbamoyl or aralkyl (especially benzyl);

$A^2$ is a lipophilic α-amino acid which contains a phenyl, mono-, di- or tri-substituted phenyl, heteroaryl or a naphthyl group, and this cyclic group is separated from the backbone of the amino acid by —CH$_2$— or —CH$_2$—CH$_2$—, (while the substituents of the phenyl group may, independently of one another, be halogen, trihalomethyl, alkoxy or alkyl);

$R^2$ and $R^3$ independently of each other denote alkyl, arylalkyl or heteroarylalkyl (wherein aryl denotes phenyl, mono-, di- or tri-substituted phenyl or naphthyl; the substituents of the phenyl group independently of one another denote halogen, trihalomethyl, alkoxy, alkyl, alkylthio, hydroxy, trifluoromethoxy, dialkylamino or cyano or 2 adjacent positions of the phenyl group are linked by —O—(CH$_2$)$_{1\,or\,2}$-O—; heteroaryl denotes indolyl, pyridyl, pyrrolyl, imidazolyl or thienyl; and the alkyl or alkoxy group contains 1 to 3 carbon atoms) or the group

denotes a ring of general formula

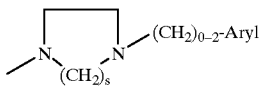

wherein s is 2 or 3, (wherein aryl denotes phenyl, mono-, di- or tri-substituted phenyl or naphthyl; the substituents of the phenyl group independently of one another denote halogen, trihalomethyl, alkoxy, alkyl, cyano, hydroxy, nitro, —CO$_2$CH$_3$, —CO$_2$C$_2$H$_5$ or alkylthio or 2 adjacent positions of the phenyl group are linked by —O—(CH$_2$)$_{1-2}$—O— and alkyl contains 1 to 3 carbon atoms).

The compounds according to the invention are valuable neurokinin (tachykinin)-antagonists which have both substance P-antagonism and neurokinin A- and neurokinin B-antagonistic properties. They are useful for the treatment and prevention of neurokinin-mediated diseases.

Compounds of general formula I may have acid groups, chiefly carboxyl groups, or phenolic hydroxy groups, and/or basic groups such as for example guanidino- or aminofunctional groups. Compounds of general formula I may therefore occur either as internal salts, as salts with pharmaceutically useful inorganic acids such as hydrochloric acid, sulphuric acid, phosphoric acid, or sulphonic acid or organic acids (such as for example maleic acid, fumaric acid, citric acid, tartaric acid or acetic acid) or as salts with pharmaceutically useful bases such as alkali or alkaline earth metal hydroxides or carbonates, zinc or ammonium hydroxides or organic amines such as for example diethylamine, triethylamine, triethanolamine and the like.

The chiral centres in the new amino acid derivatives may be of R-, S- or R,S-configuration.

The term "heteroaryl group" used in the definition of $A^2$ denotes a mono-, di- or tri-cyclic aromatic ring system which contains 1 or 2 heteroatoms, namely one or two nitrogen atoms or one nitrogen and one sulphur atom. If desired, the group may contain 1 or 2 substituents ($C_{1-3}$alkyl) or an oxo group or an alkoxy group containing 1 to 3 carbon atoms.

Examples of suitable heteroaryl groups are

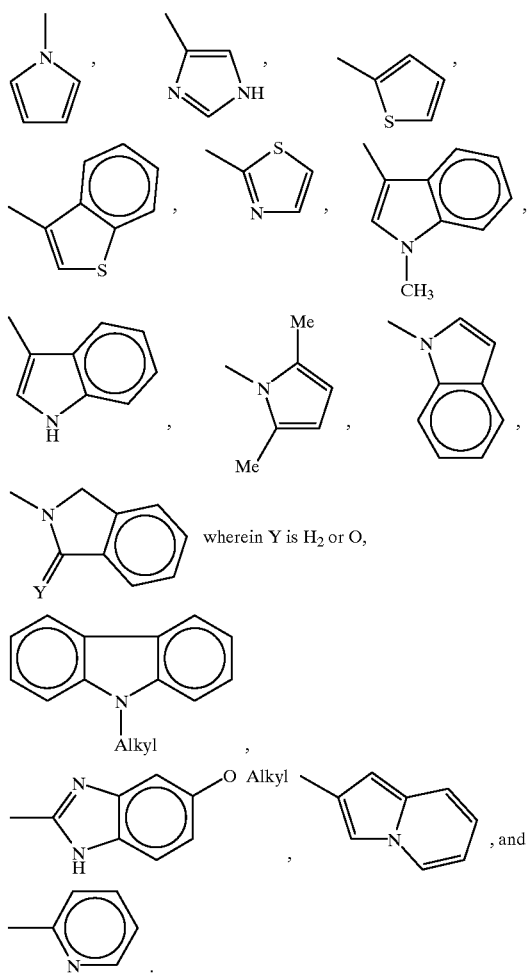

wherein Y is H₂ or O,

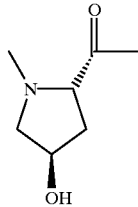

It should be noted that the heteroaryl groups mentioned above may also be bonded to the —CH₂—CH₂— group in positions other than those specified.

The —CH₂CH₂— group is bonded to the α-carbon atom of the amino acid ($A^2$).

Of the compounds of formula I according to the invention, the preferred ones are those wherein $R^1$ and $R^{11}$ are as hereinbefore defined, and $A^1$ is proline, 4-hydroxyproline or thiazolidine-4-carboxylic acid (thioproline), preferably 4-hydroxyproline of 2-S-configuration, particularly

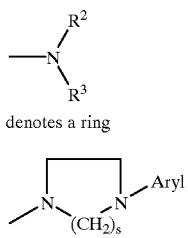

and/or $A^2$ denotes a lipophilic alpha-amino acid which contains naphthyl, indolyl or N-methylindolyl, which group is separated from the back bone of the amino acid group by —CH₂— or —CH₂—CH₂—, with $A^2$ preferably being the group

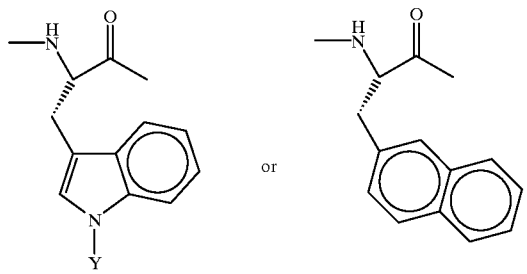

wherein Y is H or CH₃, preferably H;

and/or $R^2$ is H or methyl and $R^3$ is benzyl, the phenyl group contained therein being substituted by methyl, chlorine or bromine, preferably in the 2-position; particularly compounds wherein $R^3$ is 2-chlorobenzyl, 2-methylbenzyl or preferably 2-bromobenzyl; or those compounds wherein the group $$-\!\!-\!\!\underset{R^3}{\overset{R^2}{N}}$$

denotes a ring wherein s is 2 and aryl is as hereinbefore defined, preferably phenyl, which is substituted in the 2-position by halogen, trihalomethyl or preferably methoxy.

Of the compounds defined above, the preferred ones are those wherein $R^1$ is unsubstituted adamantyl or noradamantyl;

and those wherein $R^1$ is adamantyl or noradamantyl substituted by $X^1$, in which $X^1$ is in the 1-position when the ring in the 2-position is linked to $R^{11}$ and preferably $X^1$ is in the 3-position when the ring in the 1-position is linked to $R^{11}$, and particularly those wherein $R^1$ denotes one of the following groups

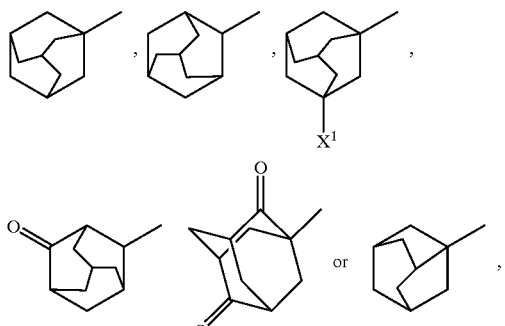

preferably those wherein R¹ is

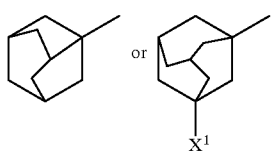

wherein X¹ is Br, C(O)NH CH₃, C(O)N(CH₃)₂ or NH₂;

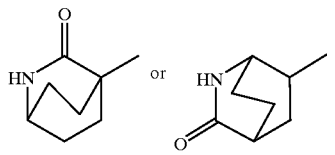

Particular mention should also be made of those compounds wherein R¹ is [2,2,2]-bicyclooctanyl which is linked to R¹¹ in the 1- or 2-position and is substituted by X² and/or by one or two oxo groups,
particularly those wherein
R¹ is one of the groups

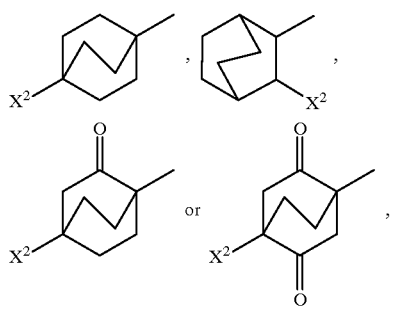

preferably wherein R¹ is one of the groups

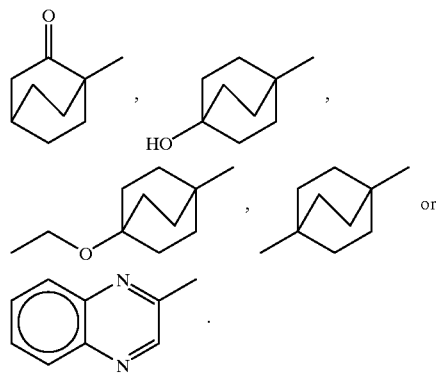

Of the compounds described above, particular mention should be made of those wherein R¹¹ is —O—C(O)— or preferably —C(O)—.

Special emphasis should be placed on the following compounds:

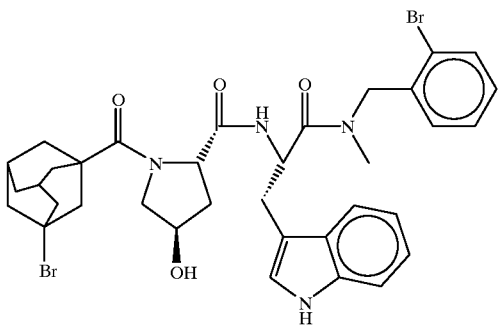

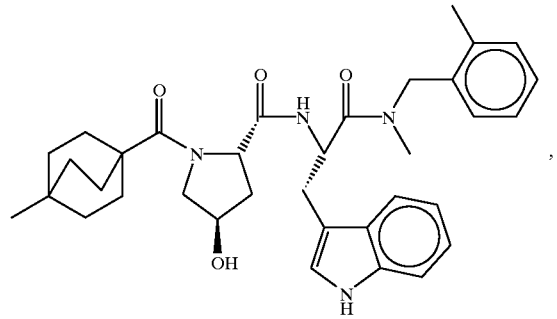

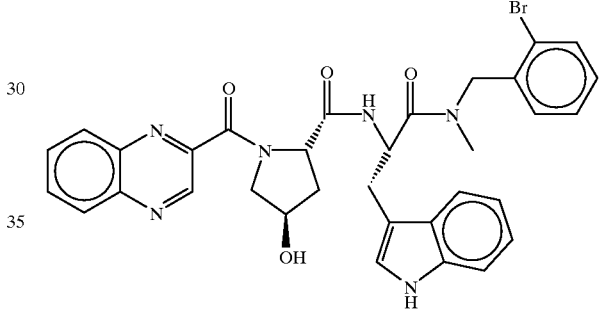

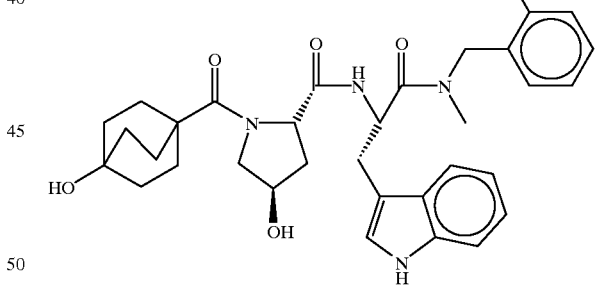

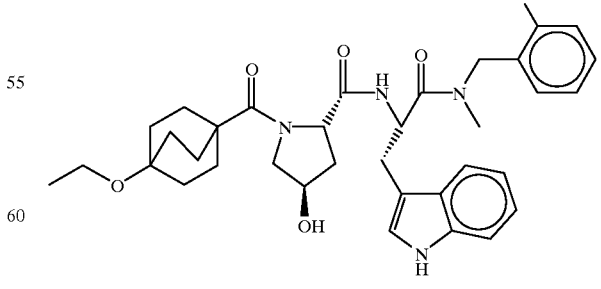

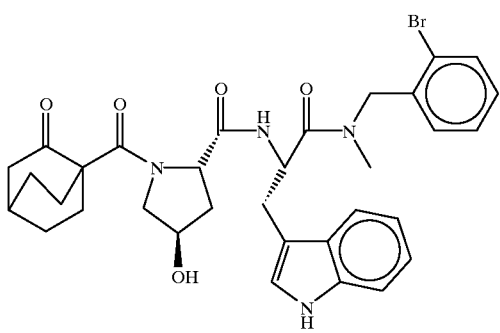

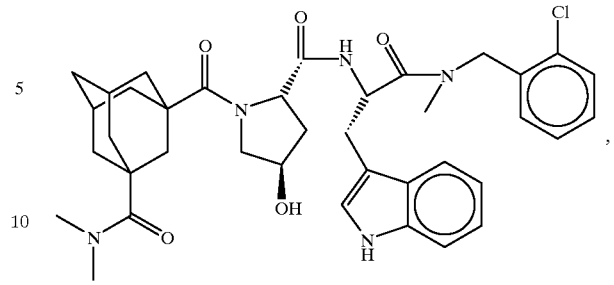

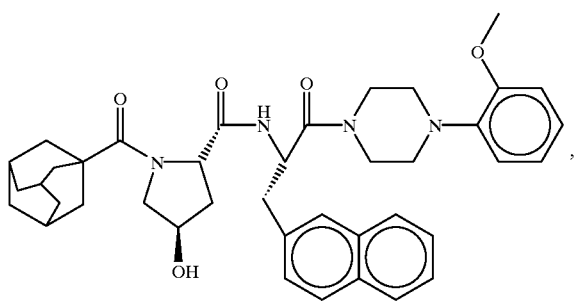

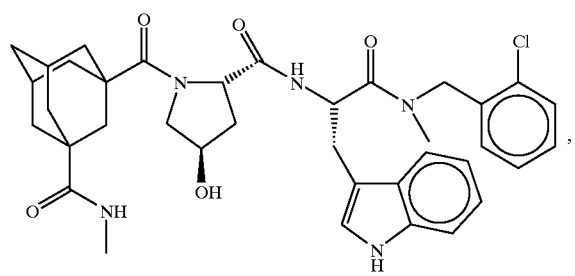

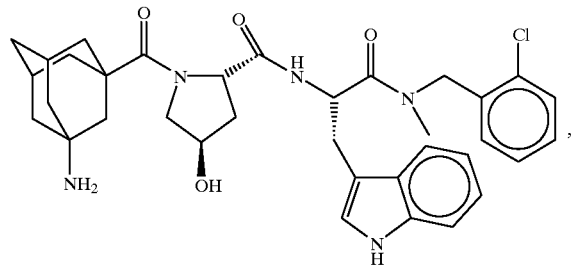

and the pharmaceutically acceptable salts thereof.

The amino acids specified are preferably in the S-configuration.

Test results for compounds according to the invention: the receptor affinity for the $NK_1$-receptor (substance P-receptor) was measured on human lymphoblastoma cells (IM-9) with cloned $NK_1$-receptors, by measuring the displacement of $^{125}$I-labelled substance P. The $NK_2$-binding test was carried out on transfected A20 cells which express the human $NK_2$-receptor. The displacement of $^{125}$I-BN-neusolinin A was determined.

The $Ki_{50}$ values thus obtained are as follows:

| Compound | $NK_1$ [nM] | $NK_2$ [nM] |
|---|---|---|
| 3 | 1 | 55 |
| 5 | 1.3 | 105 |
| 12 | 13 | 52 |
| 13 | 3 | 177 |
| 14 | 5 | 100 |
| 21 | 4.1 | 137 |
| 22 | 6.2 | 45 |
| 25 | 18.4 | |
| 36 | 1.1 | 38 |
| 47 | 0.28 | 68 |
| 52 | 0.41 | 122 |
| 59 | 0.4 | 77 |

Examples of compounds of the invention

1.)

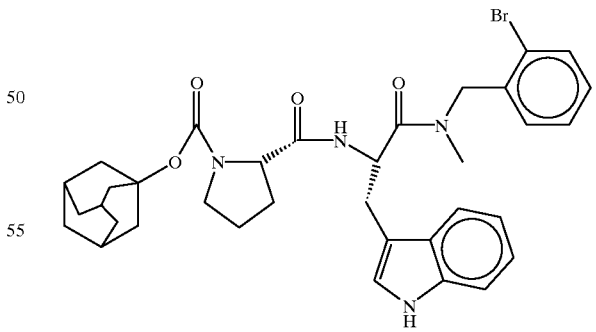

M.p.: 120–128° C.; $[\alpha]_D^{20}$ = -16.4° (DMSO)

2.)
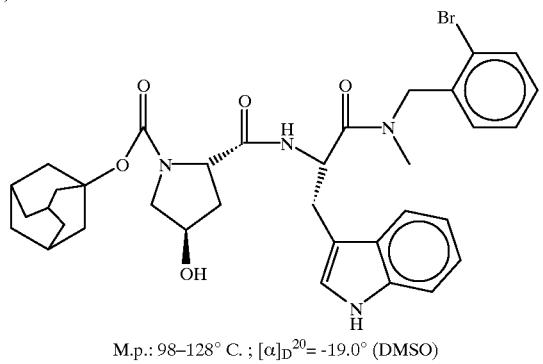
M.p.: 98–128° C. ; $[\alpha]_D^{20}$= -19.0° (DMSO)
3.)
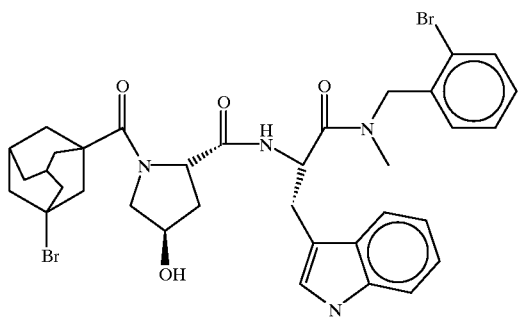
M.p.: 187–190° C. ; $[\alpha]_D^{20}$= -8.4° (DMSO)
4.)
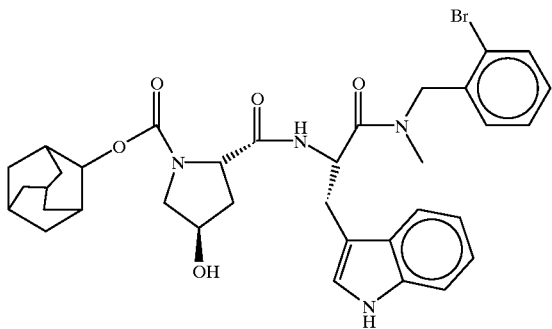
M.p.: 124–130° C. ; $[\alpha]_D^{20}$= -19.1° (DMSO)
5.)
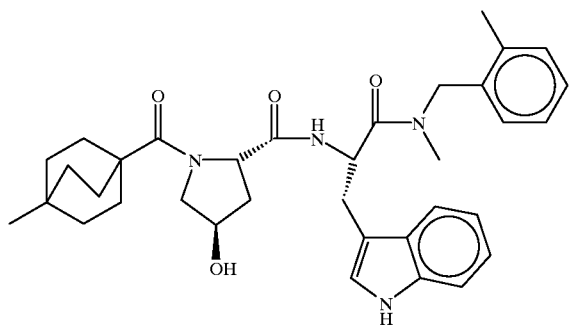
M.p.: 187–189° C. ; $[\alpha]_D^{20}$= -11.4° (DMSO)
6.)
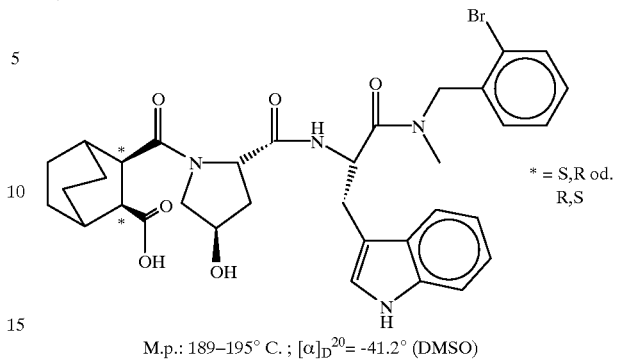
\* = S,R od. R,S
M.p.: 189–195° C. ; $[\alpha]_D^{20}$= -41.2° (DMSO)
7.)
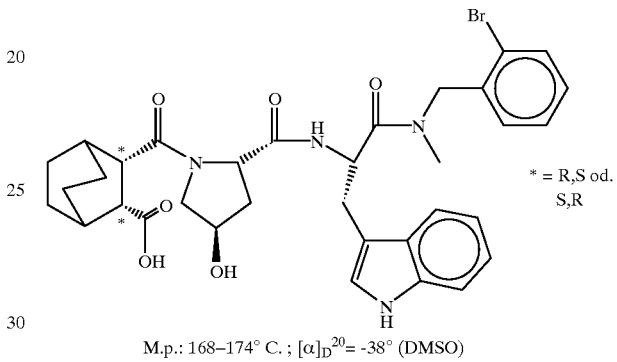
\* = R,S od. S,R
M.p.: 168–174° C. ; $[\alpha]_D^{20}$= -38° (DMSO)
8.)
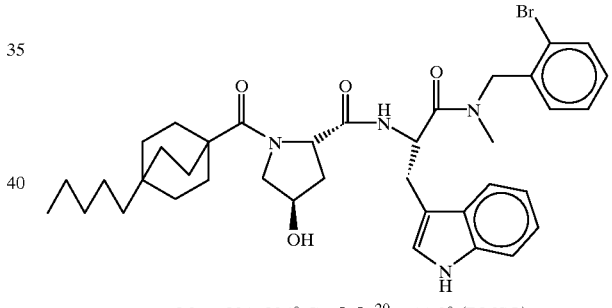
M.p.: 201–204° C. ; $[\alpha]_D^{20}$= -11.0° (DMSO)
9.)
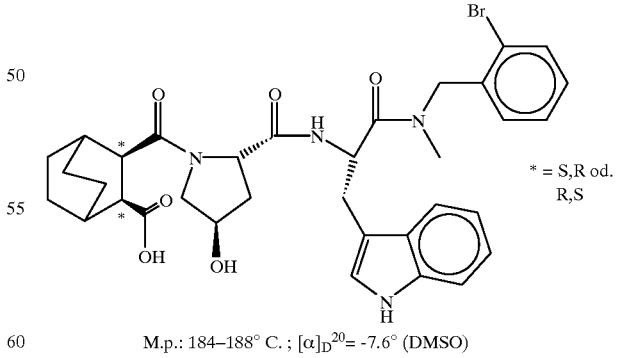
\* = S,R od. R,S
M.p.: 184–188° C. ; $[\alpha]_D^{20}$= -7.6° (DMSO)

10.)
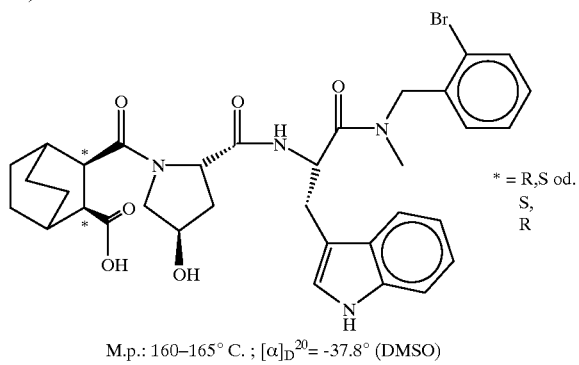
* = R,S od.
S, R
M.p.: 160–165° C.; [α]$_D^{20}$= -37.8° (DMSO)
11.)
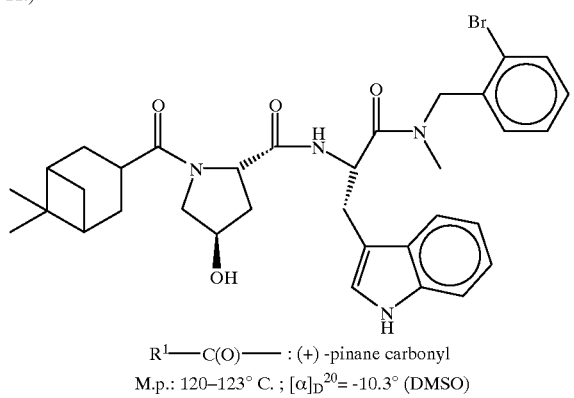
R$^1$—C(O)—: (+)-pinane carbonyl
M.p.: 120–123° C.; [α]$_D^{20}$= -10.3° (DMSO)
12.)
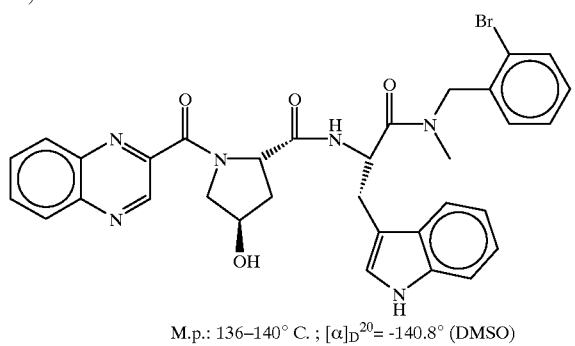
M.p.: 136–140° C.; [α]$_D^{20}$= -140.8° (DMSO)
13.)
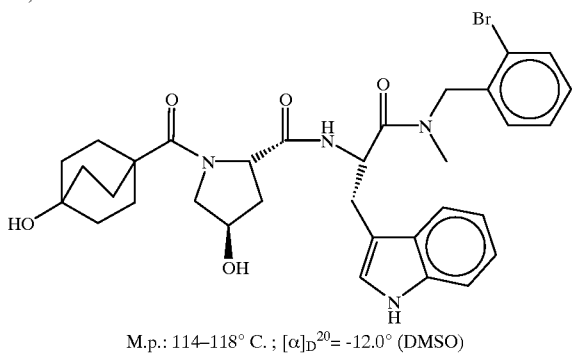
M.p.: 114–118° C.; [α]$_D^{20}$= -12.0° (DMSO)
14.)
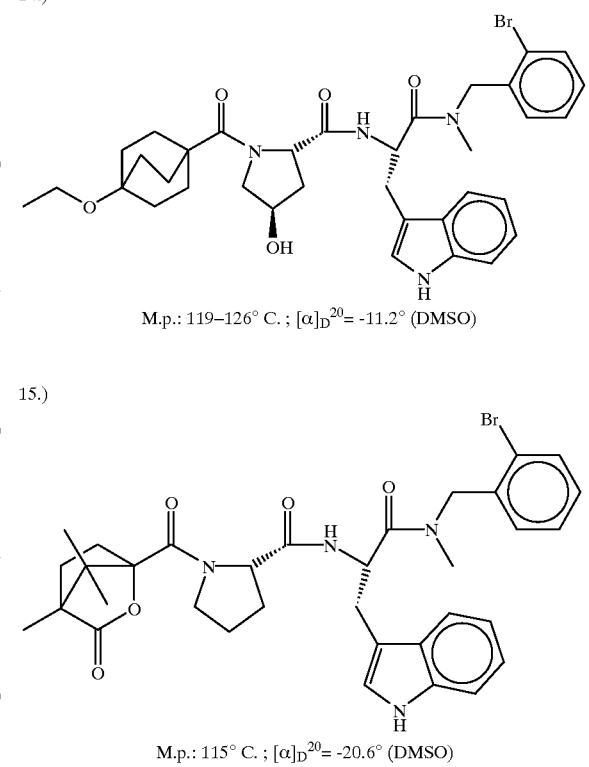
M.p.: 119–126° C.; [α]$_D^{20}$= -11.2° (DMSO)
15.)
M.p.: 115° C.; [α]$_D^{20}$= -20.6° (DMSO)
16.)
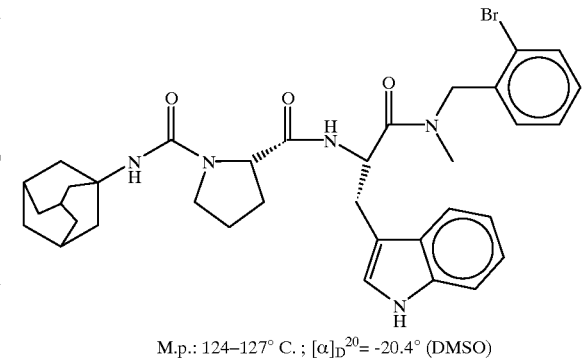
M.p.: 124–127° C.; [α]$_D^{20}$= -20.4° (DMSO)
17.)
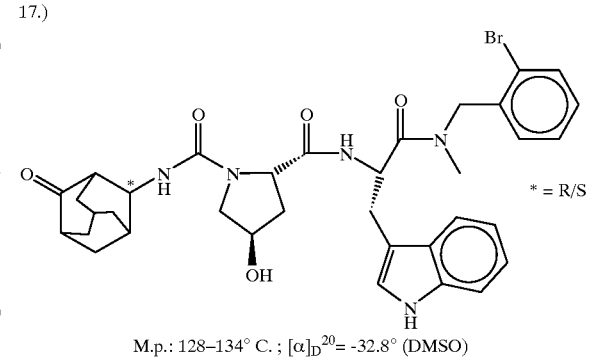
* = R/S
M.p.: 128–134° C.; [α]$_D^{20}$= -32.8° (DMSO)

-continued
18.)
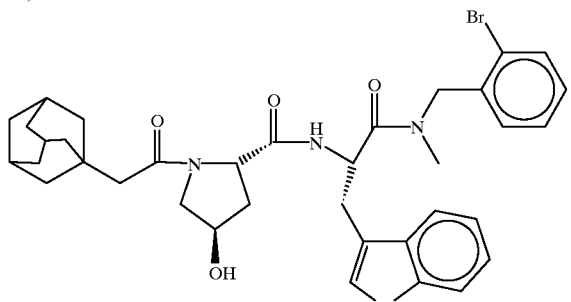
M.p.: 120–127° C. ; [α]$_D^{20}$= -25° (DMSO)
19.)
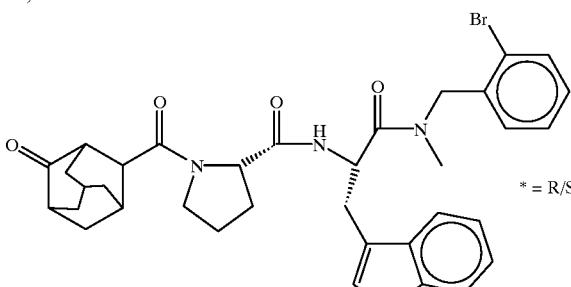
* = R/S
M.p.: 128–134° C. ; [α]$_D^{20}$= -35.6° (DMSO)
20.)
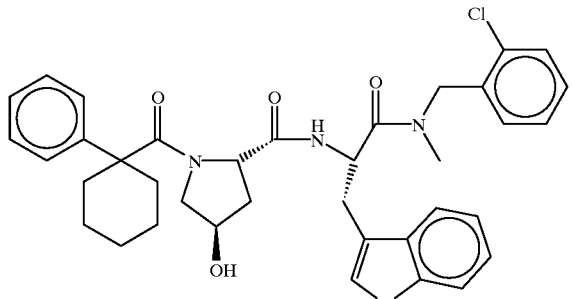
M.p.: 130–136° C. ; [α]$_D^{20}$= -26.2° (DMSO)
21.)
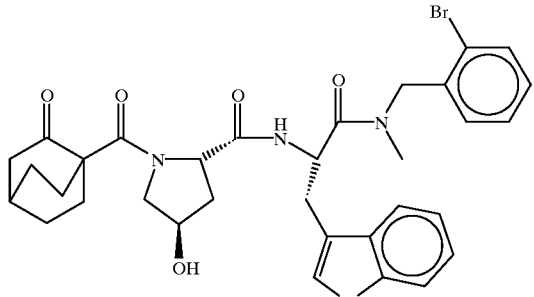
M.p.: 143° C. ; [α]$_D^{20}$= -4.8° (DMSO)
-continued
22.)
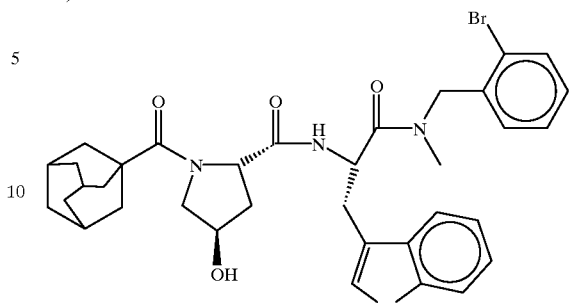
M.p.: 160–165° C. ; [α]$_D^{20}$= -7.0° (DMSO)
23.)
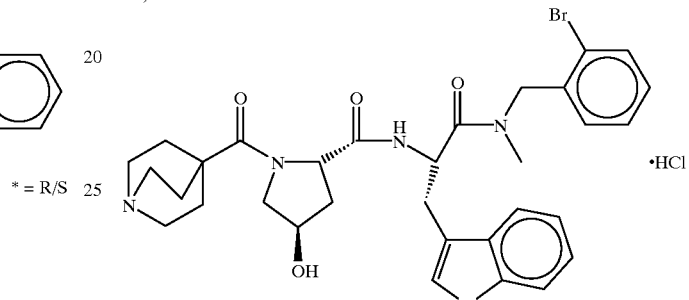
·HCl
M.p.: 196–201° C. ; [α]$_D^{20}$= -11.8° (DMSO)
24.)
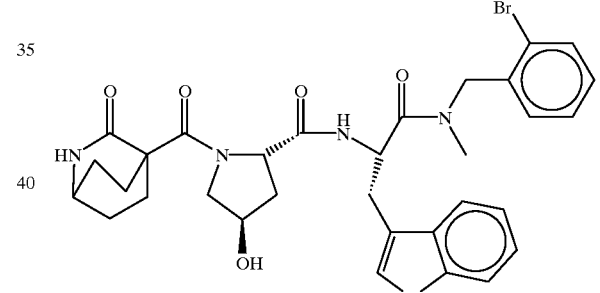
M.p.: 158–162° C. ; [α]$_D^{20}$= -10.8° (DMSO)
25.)
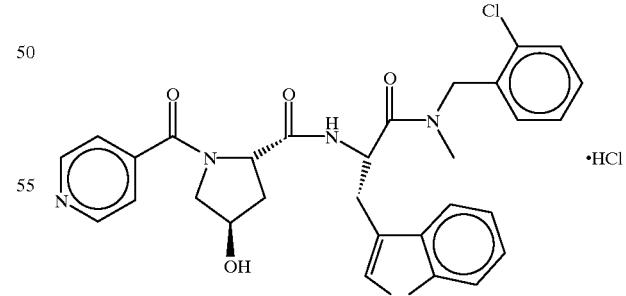
·HCl
M.p.: 146–148° C. ; [α]$_D^{20}$= -64.8° (DMSO)

26.)
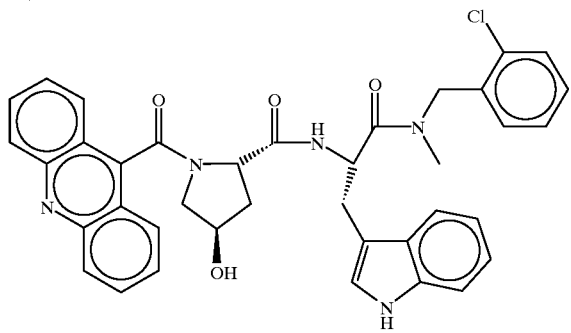
27.)
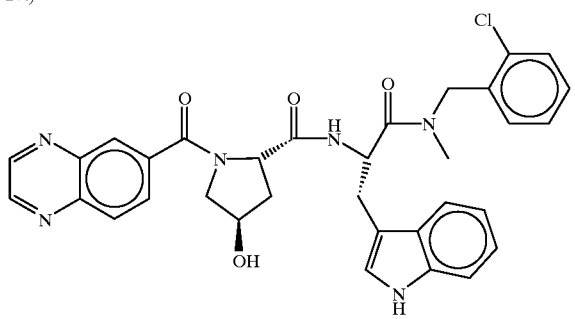
M.p.: 123–126° C. ; [α]$_D^{20}$= -86.8° (DMSO)
28.)
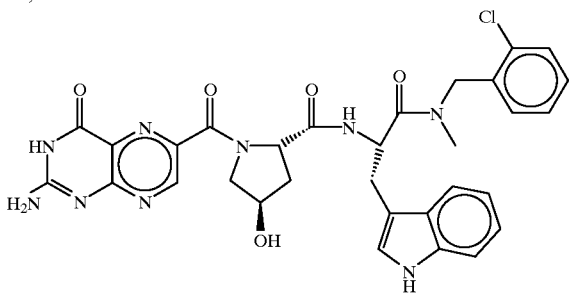
29.)
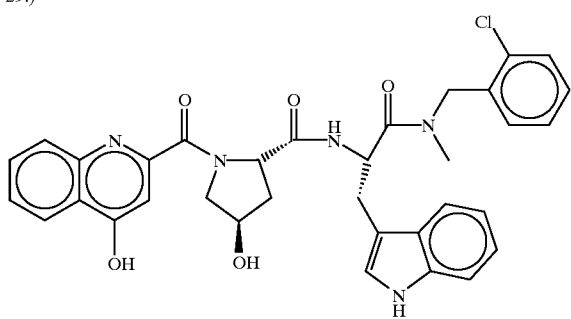
M.p.: 172–177° C. ; [α]$_D^{20}$= -70.4° (DMSO)
30.)
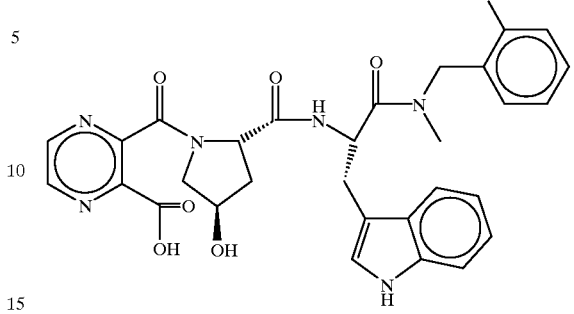
M.p.: 170 (dec.); [α]$_D^{20}$= -70.4° (DMSO)
31.)
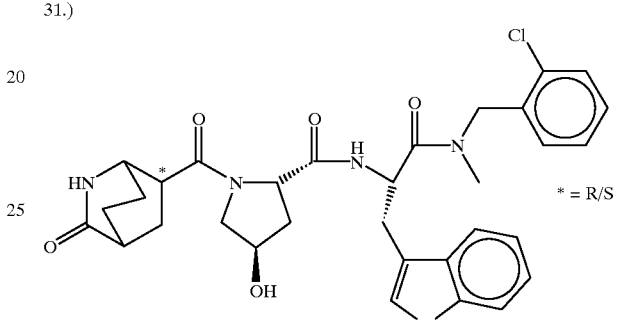
* = R/S
32.)
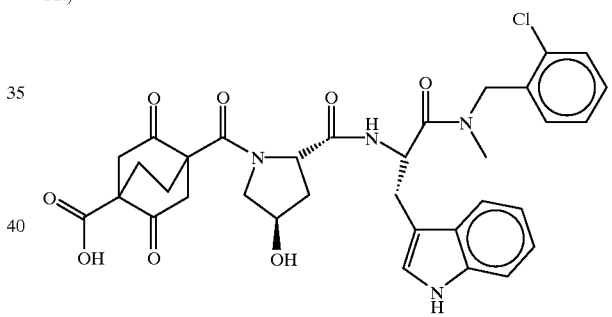
33.)
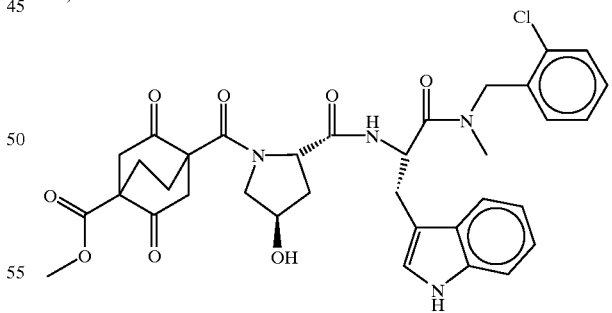

34.)
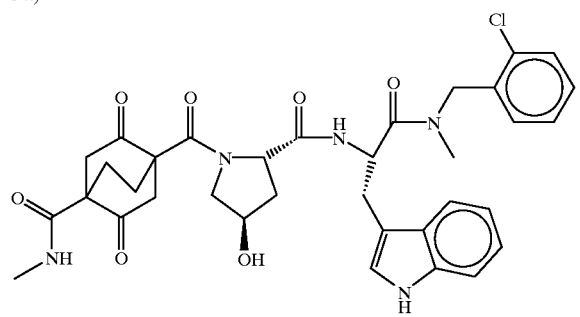
35.)
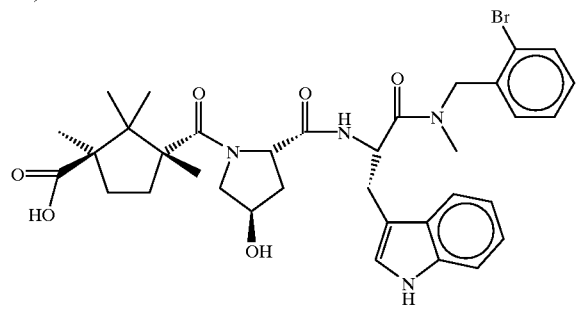
36.)
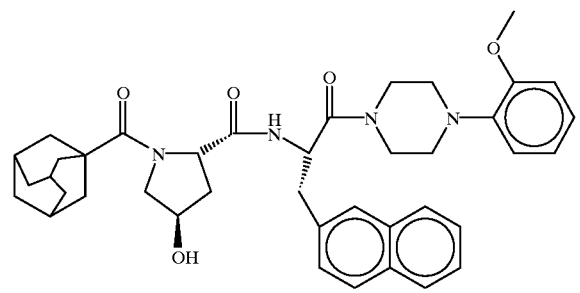
M.p.: 171–178° C.; [α]$_D^{20}$= -37.4° (DMSO)
37.)
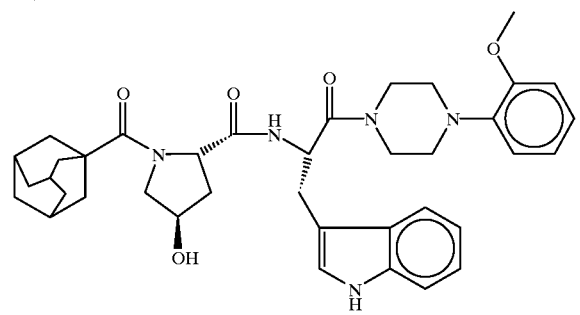
38.)
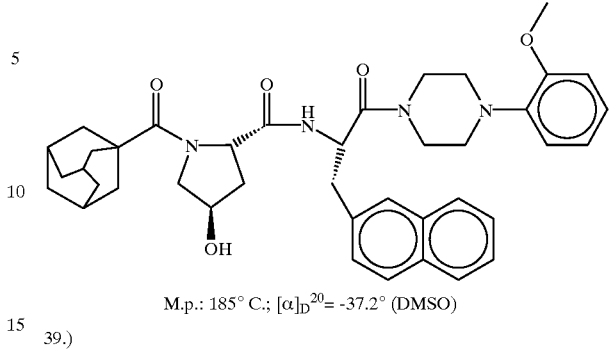
M.p.: 185° C.; [α]$_D^{20}$= -37.2° (DMSO)
39.)
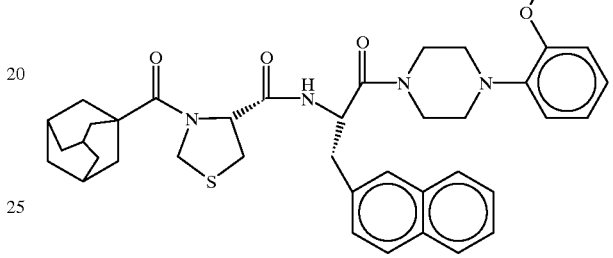
40.)
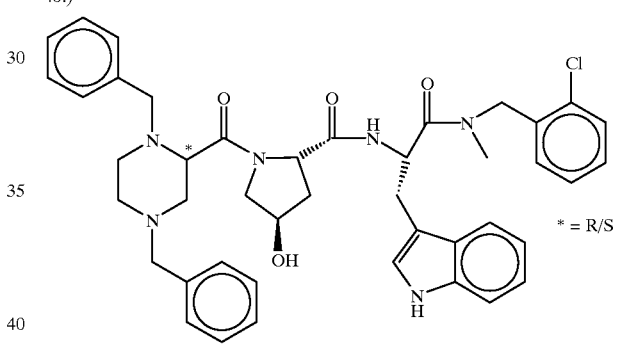
* = R/S
M.p.: 126–128°C.; [α]$_D^{20}$= -15.8° (DMSO)
41.)
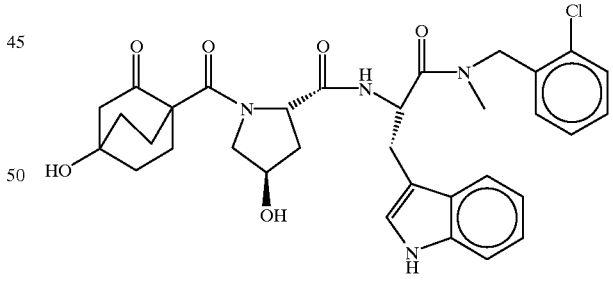
42.)
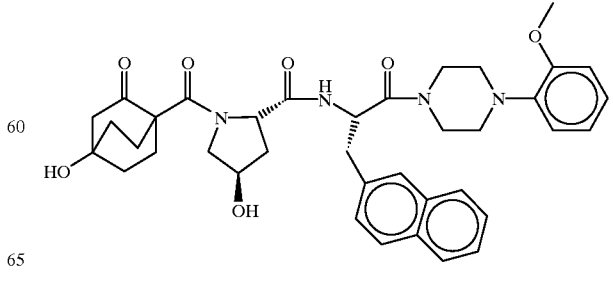

43.)
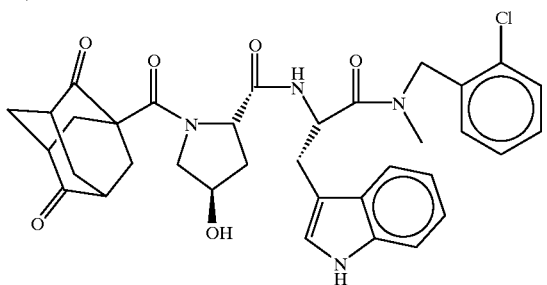
44.)
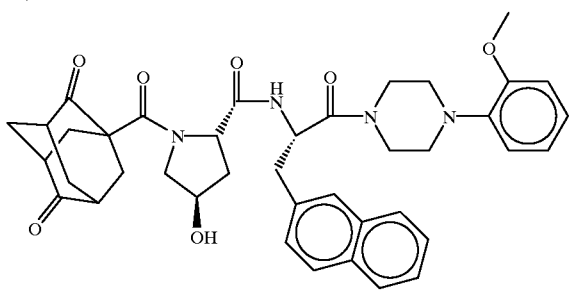
45.)
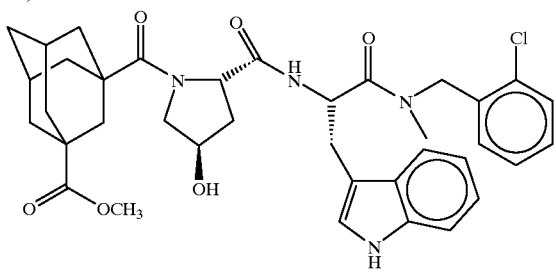
M.p.: 198–200°C. $[\alpha]_D^{20}$= -5.8° (DMSO)
46.)
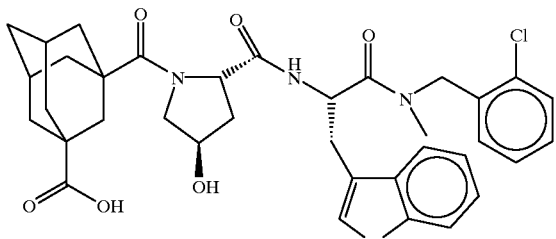
M.p.: 200–204°C. $[\alpha]_D^{20}$= -7° (DMSO)
47.)
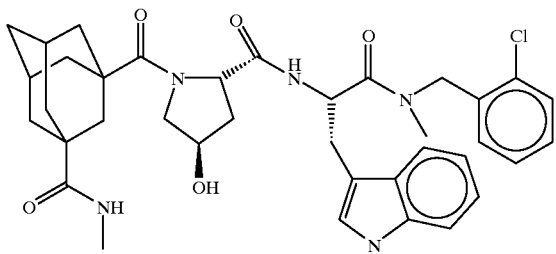
M.p.: 120–125°C. $[\alpha]_D^{20}$= -5.4° (DMSO)
48.)
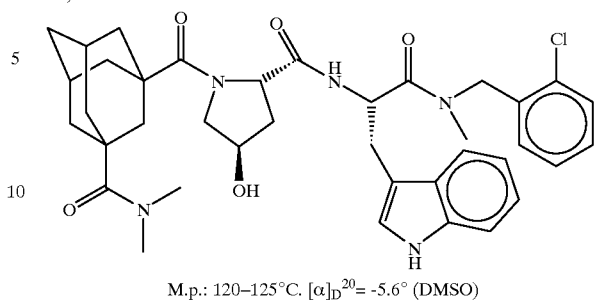
M.p.: 120–125°C. $[\alpha]_D^{20}$= -5.6° (DMSO)
49.)
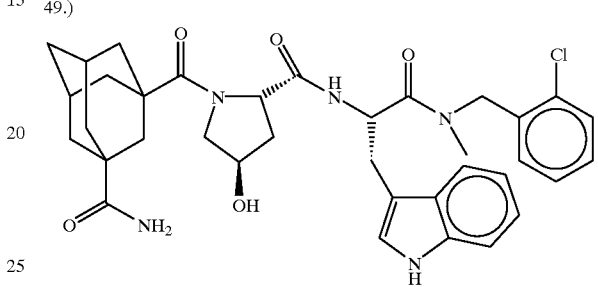
M.p.: 142–147°C. $[\alpha]_D^{20}$= -1.8° (DMSO)
50.)
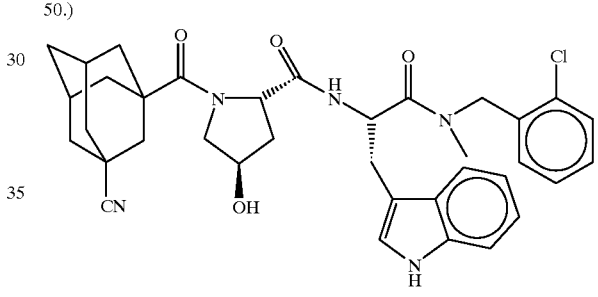
51.)
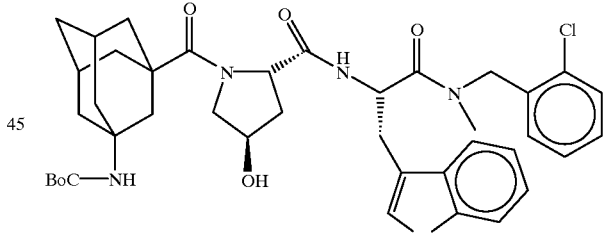
M.p.: 146–148°C. $[\alpha]_D^{20}$= -3.8° (DMSO)
52.)
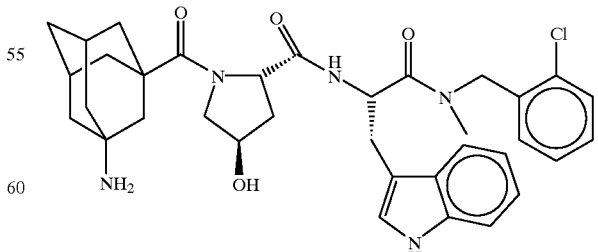
M.p.: 198–202°C. $[\alpha]_D^{20}$= -7.4° (DMSO)

53.)
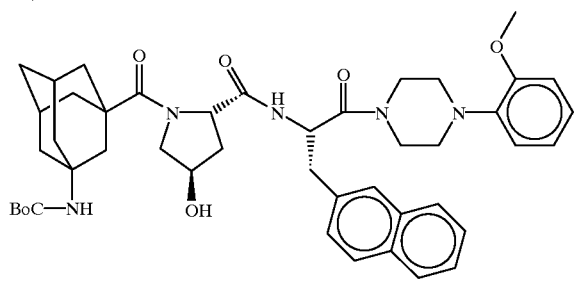
M.p.: 130–138°C. [α]$_D^{20}$= -30° (DMSO)
54.)
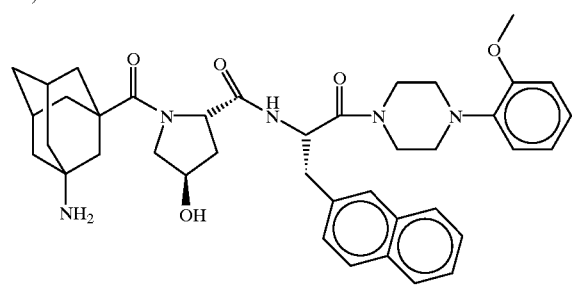
M.p.: 194–197°C. [α]$_D^{20}$= -30° (DMSO)
55.)
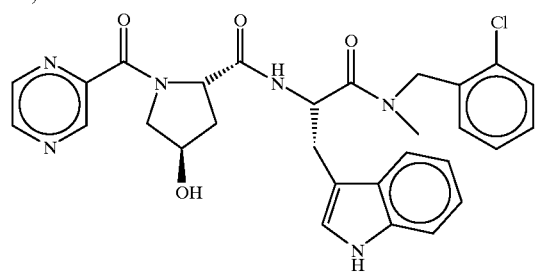
56.)
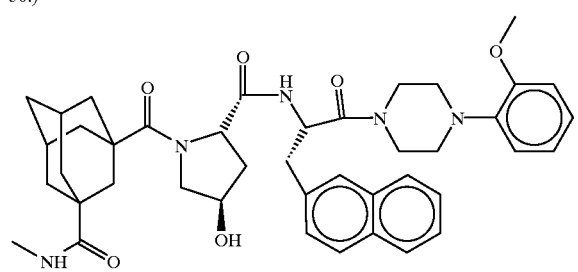
M.p.: 122–127°C. [α]$_D^{20}$= -35° (DMSO)
57.)
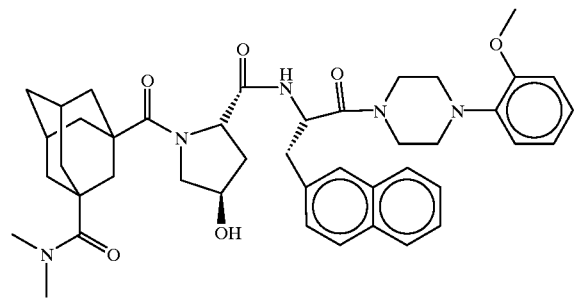
M.p.: 116–122°C. [α]$_D^{20}$= -33.4° (DMSO)
58.)
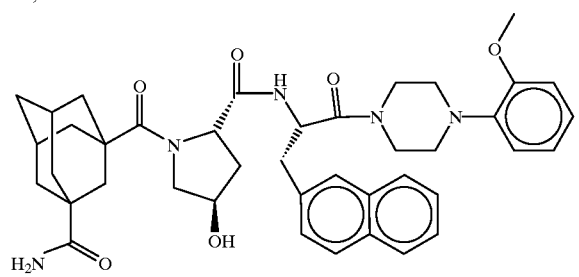
M.p.: 130–138°C. [α]$_D^{20}$= -31.6° (DMSO)
59.)
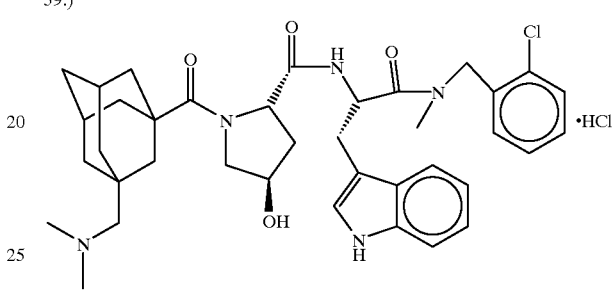
M.p.: 128–138°C. [α]$_D^{20}$= -6.6° (DMSO)
60.)
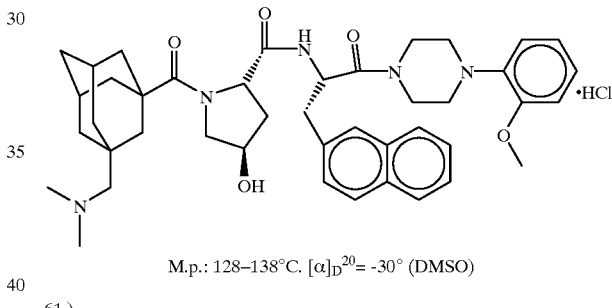
M.p.: 128–138°C. [α]$_D^{20}$= -30° (DMSO)
61.)
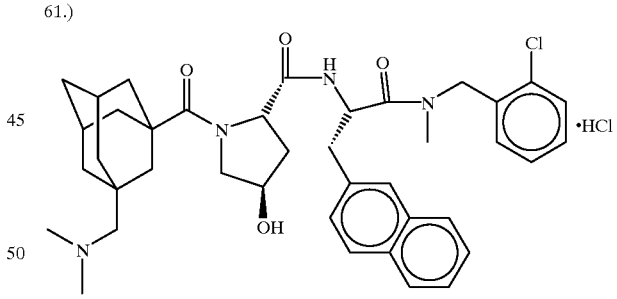
M.p.: 130–135°C. [α]$_D^{20}$= -18° (DMSO)
62.)
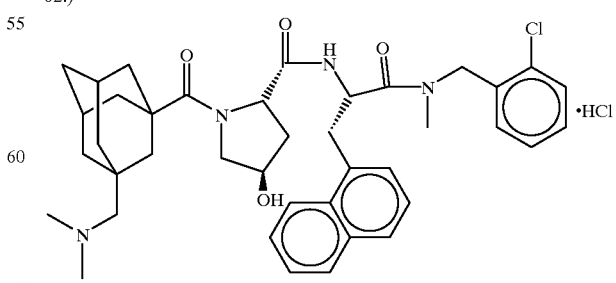
M.p.: 130–135°C. [α]$_D^{20}$= 0° (DMSO)

63.)
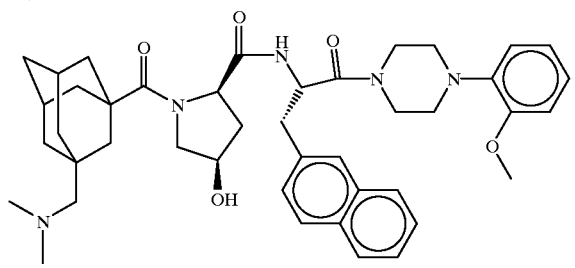
M.p.: 103–106°C. $[\alpha]_D^{20} = -45.4°$ (DMSO)
64.)
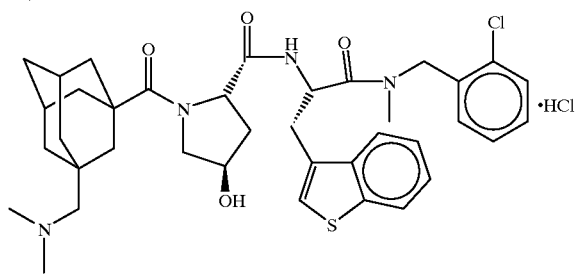
M.p.: 129–136°C. $[\alpha]_D^{20} = -17.6°$ (DMSO)
65.)
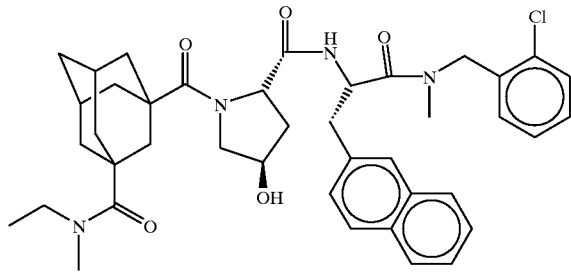
M.p.: 94–98°C. $[\alpha]_D^{20} = -19.4°$ (DMSO)
66.)
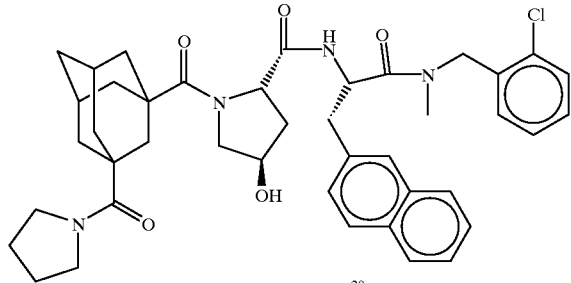
M.p.: 107–110°C. $[\alpha]_D^{20} = -18.4°$ (DMSO)
67.)
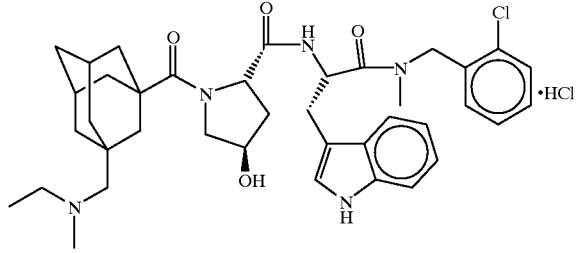
M.p.: 126–128°C. $[\alpha]_D^{20} = -8°$ (DMSO)
68.)
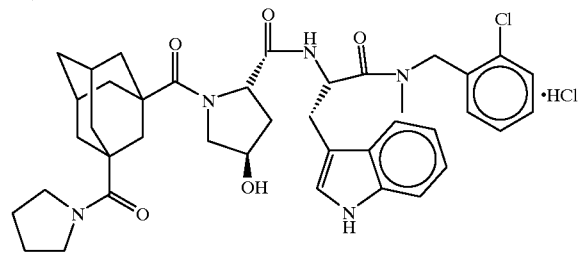
M.p.: 153–158°C. $[\alpha]_D^{20} = -7.8°$ (DMSO)
69.)
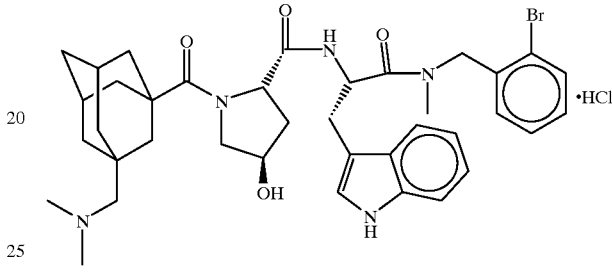
M.p.: 153–163°C. (decomp.) $[\alpha]_D^{20} = -8.2°$ (DMSO)
70.)
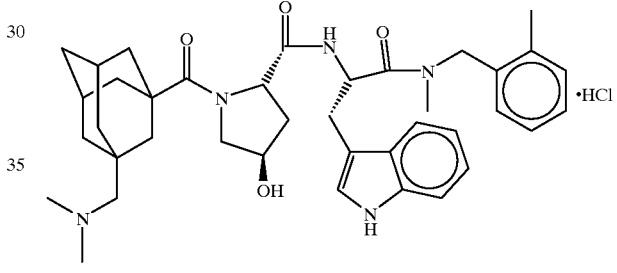
M.p.: 156–164°C. (decomp.) $[\alpha]_D^{20} = -9.4°$ (DMSO)
71.)
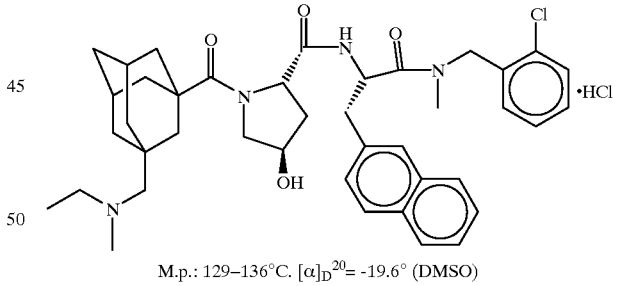
M.p.: 129–136°C. $[\alpha]_D^{20} = -19.6°$ (DMSO)
72.)
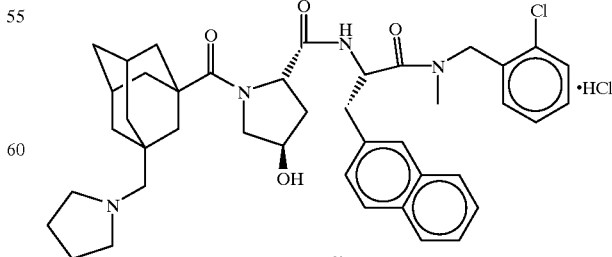
M.p.: 139–146°C. $[\alpha]_D^{20} = -18.6°$ (DMSO)

73.)

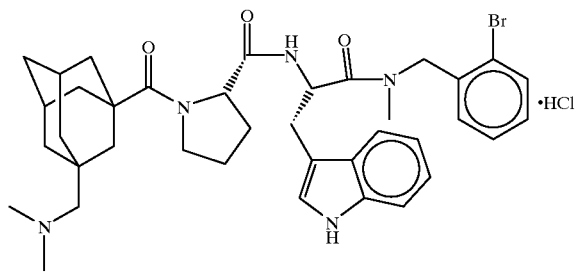

M.p.: 129–135°C. $[\alpha]_D^{20}= -17.4°$ (DMSO)

74.)

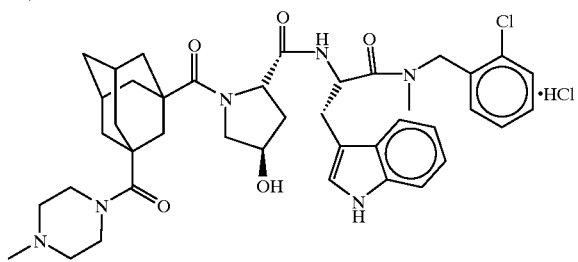

M.p.: 172–176°C. $[\alpha]_D^{20}= -7.8°$ (DMSO)

75.)

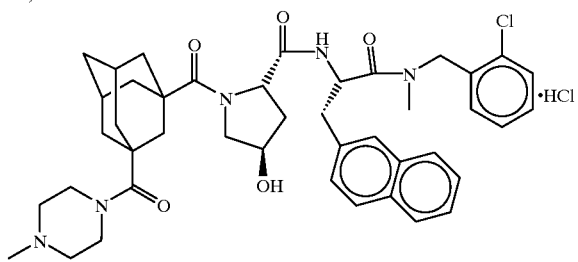

M.p.: 138–145°C. $[\alpha]_D^{20}= -18.4°$ (DMSO)

76.)

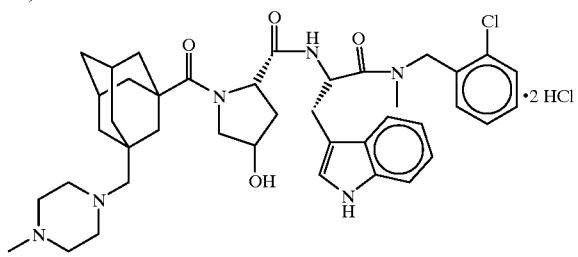

M.p.: 181–187°C. $[\alpha]_D^{20}= -7.2°$ (DMSO)

77.)

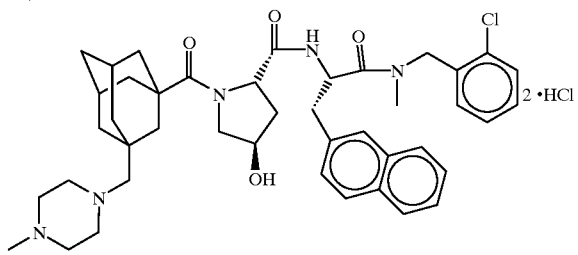

M.p.: 150–155°C. $[\alpha]_D^{20}= -18°$ (DMSO)

Of these compounds, compounds 3, 5, 12, 13, 14, 21, 22, 36, 47, 52 and 59 are preferred.

In representing the above formulae, the CH$_3$ groups have not been written out. Compound 1, for example, contains a methyl group as R$^2$ in the group NR$^2$R$^3$.

The compounds according to the invention are valuable neurokinin (tachykinin)-antagonists which have both substance P-antagonism and also neurokinin A- and neurokinin B-antagonistic properties. They are useful for treating and preventing neurokinin-mediated diseases:

For treating or preventing inflammatory and allergic diseases of the respiratory tract, such as asthma, chronic bronchitis, hyper-reactive respiratory tract, emphysema, rhinitis, cough, of the eyes, such as conjunctivitis and iritis, of the skin, such as dermatitis in contact eczema, urticaria, psoriasis, sun burn, insect bites, itching, sensitive or hyper-sensitive skin, of the gastrointestinal tract such as gastric and duodenal ulcers, ulcerative colitis, Crohn's disease, irritable bowel and Hirschsprung's disease, of the joints, such as rheumatoid arthritis, reactive arthritis and Reiter syndrome;

for treating diseases of the central nervous system such as dementia, Alzheimer's disease, schizophrenia, psychosis, depression, headaches (e.g. migraine or tension headaches), epilepsy;

treatment of Herpes zoster and post-herpetic pain, tumour, collagenosis, dysfunction of the deferent urinary tract, haemorrhoids, nausea and vomiting, triggered for example by radiation or cytostatic therapy or motion and pain of all types.

Particularly interesting from a medical point of view are compounds in which the NK$_1$- and NK$_2$-values are of a similar order of magnitude.

The invention therefore also relates to the use of the compounds according to the invention as curative agents and pharmaceutical preparations which contain these compounds. They are preferably administered to humans. The compounds according to the invention may be administered by intravenous, subcutaneous, intramuscular, intraperitoneal or intranasal route, by inhalation, transdermally, optionally promoted by iontophoresis or enhancers known from the literature, and by oral route.

For parenteral use the compounds of formula I or the physiologically acceptable salts thereof are dissolved, suspended or emulsified, optionally with the conventional substances for this purpose such as solubilisers, emulsifiers or other excipients. Examples of solvents include: water, physiological saline solutions or alcohols, e.g. ethanol, propanediol or glycerol, sugar solutions such as glucose or mannitol solutions or a mixture of various solvents.

In addition, the compounds may be administered by means of implants, e.g. of polylactide, polyglycolide or polyhydroxybutyric acid or in the form of intranasal preparations.

The compounds according to the invention may be prepared by methods generally known in amino acid and peptide chemistry, by condensing the amino acids, acids and amines step-by-step. The resulting compound may be isolated either in free form or, if desired, in the form of a salt.

The amino acid derivatives of formula I according to the invention

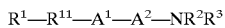

may be made up of the components R$^1$—R$^{11}$OH, H—A$^1$—OH, H—A$^2$—OH and HN(R$^3$)R$^2$, whilst the coupling sequence may pass from right to left, from left to right or by coupling the units $R^1$—$R^{11}$—$A^1$—OH and H—$A^2$—N($R^3$) $R^2$ (fragment couplings).

The compounds according to the invention may be prepared by generally known methods of peptide chemistry as described, for example, in "Houben-Weyl, Methoden der organischen Chemie, Volume 15/2" or by solid phase peptide synthesis (e.g. R. C. Sheppard, Int. J. Pept. Prot. Res., 21, 118 [1983]) or equivalent known methods. The amino acids or partial amino acid sequences in question are condensed step-by-step and the resulting peptides are isolated in free form or in the form of the desired salts. The amino protecting groups used are those described in "Houben-Weyl, Methoden der organischen Chemie, Volume 15/1", whilst in conventional methods of synthesis the benzyloxycarbonyl group (Z) is preferred and in solid phase synthesis the fluorenylmethoxycarbonyl group (Fmoc) is preferred. In the case of conventional synthesis, the side chain of the arginine is protected by protonation whilst in the case of solid phase synthesis the Mtr group was used. In the solid phase peptide synthesis, side chain-protected amino acids are also used; their protecting groups are, for example, t-butoxycarbonyl, N($\pi$)-tert.butyoxymethyl, butyl and tert-.butyl. The special conditions of synthesis can be inferred from the Example which follows.

In order to synthesise the compounds of general formula I using solid phase synthesis, first the dipeptide carboxylic acids are synthesised, which are converted in solution to the dipeptide amides. The following are suitable as anchor groups:

1. Benzylester (G. Barang, R. B. Merrifield, Peptides 2, 1 (1980) Eds. E. Gross, J. Meienhofer, Academic Press, New York)
2. PAM-anchor (R. B. Merrifield, J. Am. Chem. Soc. 85, 2149 (1966))
3. Wang-anchor (S.-S. Wang, J. Am. Chem. Soc. 95, 1328 (1973))
4. SASRIN-anchor (M. Mergler, R. Tanner, J. Gostuli, P. Grogg, Tetrah. Lett. 29, 4005 (1988)).

EXAMPLE (Compound 22)

Diagram of synthesis

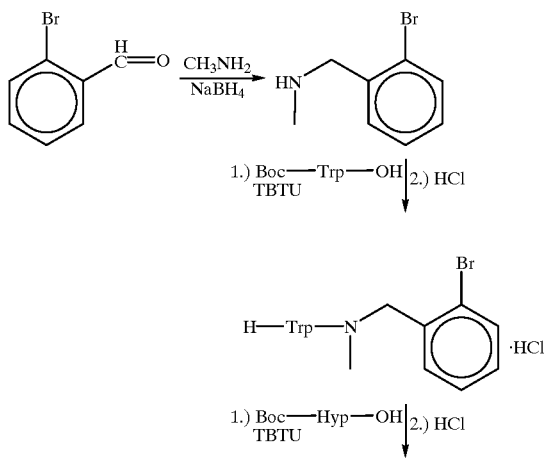

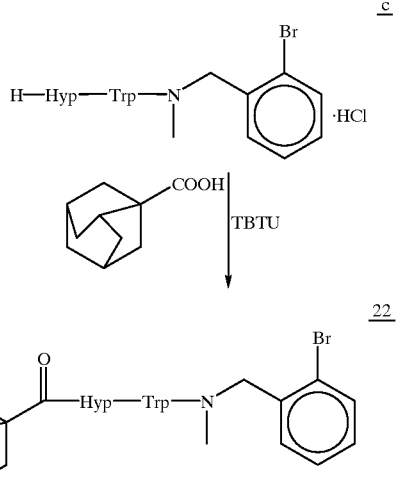

Preparation of a:

29.4 g of o-Bromobenzaldehyde and 81 ml of aqueous, 40% methylamine solution are combined with 238 ml of THF and at RT 19 g of $NaBH_4$ are added in batches within 25 minutes. The mixture is left to stand overnight at RT, concentrated using a rotary evaporator, and the residue is stirred into ice water. The aqueous phase is extracted twice with ether and the combined ether phases are evaporated down under reduced pressure. After chromatography on silica gel with ethyl acetate or ethyl acetate/methanol (4:1) as eluant, 18.5 g of N-methyl-2-bromobenzylamine (a) are obtained in the form of a yellowish liquid. Yield: 58%.

Preparation of b:

18.4 g of Boc-Trp-OH, 12.1 g of a and 20.4 g of TBTU are dissolved in 430 ml of DMF, mixed with 17.5 ml of TEA and the mixture is stirred for 1 hour at RT. The reaction mixture is poured into 3 liters of semi-concentrated $NaHCO_3$ solution and the precipitate formed is removed by suction filtering. It is dissolved in about 400 ml of $CH_2Cl_2$, separated from the residual water precipitated and evaporated down using the rotary evaporator. The residue (about 28.6 g) is mixed with about 290 ml of 4N HCl in dioxane and 29 ml of anisole, homogenised by brief treatment in an ultrasound bath and left to stand for 45 min. at RT. It is concentrated by evaporation under reduced pressure, the residue is stirred with ether, suction filtered, washed with ether and dried. 25.9 g of H-Trp-N(Me)-2-bromobenzylamide hydrochloride (b) are obtained in the form of beige crystals. Yield: 97%.

Preparation of c:

12.5 g of b, 6.84 g of Boc-Hyp-OH, 10.4 g of TBTU, 10 ml of TEA and 250 ml of DMF are combined and stirred for 3 hours at RT. The reaction mixture is stirred into a mixture of 0.5 l of saturated $NaHCO_3$ solution and 2.2 l of water, the precipitate formed is suction filtered, washed with water and dried in the desiccator. The solid white substance (15.6 g) is combined with 130 ml of 4N HCl and 13 ml of anisole, homogenised in an ultrasound bath and left to stand for 75 min. at RT. It is concentrated using a Rotavapor, the residue is stirred with ether, suction filtered, washed with ether and dried. 13.8 g of H-Hyp-Trp-N(Me)-2-bromobenzylamide hydrochloride (c) are obtained in the form of beige crystals. Yield: 87%.

Preparation of 22:

0.17 g of 3-Noradamantane carboxylic acid, 0.54 g of c, 0.3 ml of TEA, 0.35 g of TBTU and 15 ml of DMF are combined, the pH is adjusted to 8–8.5 by the addition of further TEA and the mixture is left to stand for 135 min. at RT. The reaction mixture is stirred into 150 ml of semi-concentrated NaHCO$_3$ solution and the precipitate formed is suction filtered, washed with water and dried in the desiccator. The crude substance obtained is chromatographed over a silica gel column using ethyl acetate/methanol (4:1). After concentration, digestion with ether, suction filtering, washing with ether and drying, 0.28 g of 3-noradamantane carbonyl-Hyp-Trp-N(Me)-2-bromobenzylamide (22) is obtained in the form of beige crystals. Yield: 43%.

M.p.: 160–165° C.; $[\alpha]_D^{20} = -7.0°$ (DMSO)

| Pharmaceutical Preparations: | | |
|---|---|---|
| Injectable solution | | |
| 200 mg of active substance* | | |
| 1.2 mg of monopotassium dihydrogen phosphate = KH$_2$PO$_4$ | ) | |
| 0.2 mg of disodium hydrogen phosphate = NaH$_2$PO$_4$.2H$_2$O | ) (buffer) | |
| 94 mg sodium chloride | ) (isotonic) | |
| or | ) | |
| 520 mg glucose | ) | |
| 4 mg albumin | (protease protection) | |
| q.s. sodium hydroxide solution | ) | |
| q.s. hydrochloric acid | ) up to pH 6 | |
| made up to 10 ml with water for injections | | |
| Injectable solution | | |
| 200 mg active substance* | | |
| 94 mg sodium chloride | | |
| or | | |
| 520 mg glucose | | |
| 4 mg albumin | | |
| q.s. sodium hydroxide solution | ) | |
| q.s. hydrochloric acid | ) up to pH 9 | |
| made up to 10 ml with water for injections | | |
| Lyophilisate | | |
| 200 mg of active substance* | | |
| 520 mg of mannitol (isotonic/structural component) | | |
| 4 mg albumin | | |
| Solvent 1 for lyophilisate | | |
| 10 ml of water for injections | | |
| Solvent 2 for lyophilisate | | |
| 26 mg of Polysorbate ® 80 = Tween ® 80 (surfactant) | | |
| made up to 10 ml with water for injections | | |
| *Active substance: compounds according to the invention, e.g. that of Example 22. | | |
| Dose for human weighing 67 kg: 1 to 500 mg | | |

What is claimed is:
1. A compound selected from the group consisting of:

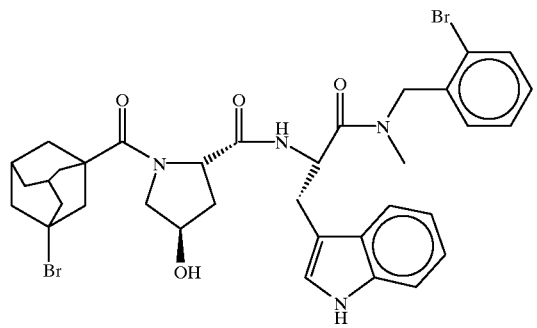

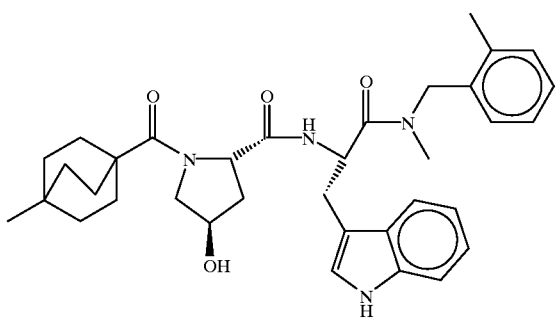

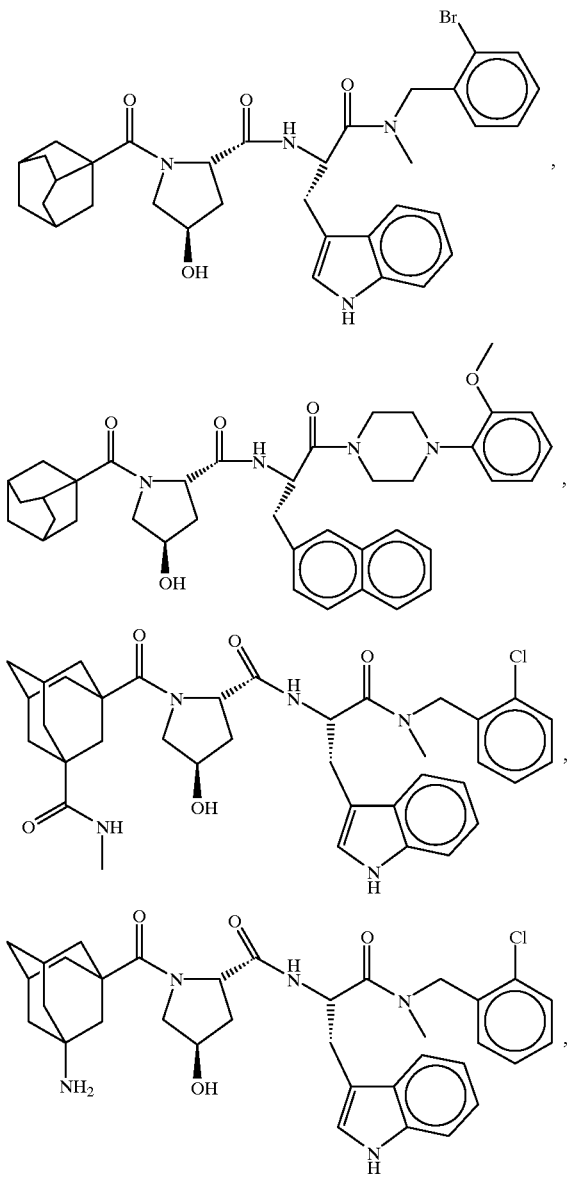

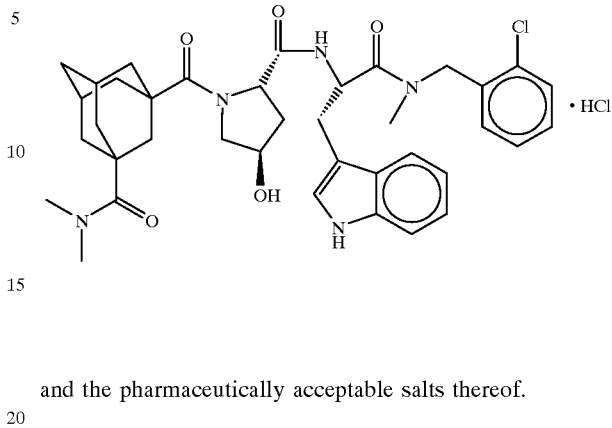

and the pharmaceutically acceptable salts thereof.

2. A pharmaceutical preparation comprising a compound according to claim 1, in admixture with a pharmaceutically acceptable carrier, diluent or excipient.

3. A method for treating or preventing a neurokinin-mediated disease which comprises administering to a host a therapeutic or prophylactic amount of a compound in accordance with claim 1.

4. A method for treating or preventing inflammation which comprises administering to a host a therapeutic or prophylactic amount of a compound in accordance with claim 1.

5. A method for treating or preventing an allergic response which comprises administering to a host a therapeutic or prophylactic amount of a compound in accordance with claim 1.

* * * * *